United States Patent
Fauron et al.

(10) Patent No.: US 6,346,612 B1
(45) Date of Patent: Feb. 12, 2002

(54) METHOD FOR IDENTIFYING DIFFERENT MAIZE CYTOTYPES AND FOR MEASURING THE CONTAMINATION OF MALE-FERTILE SEEDS MIXED WITH MALE-STERILE SEEDS

(75) Inventors: Christiane Fauron, Salt Lake City, UT (US); Jean-Michel Grienenberger, Strasbourg (FR)

(73) Assignees: The University of Utah, Salt Lake City, UT (US); Centre National de la Recherche Scientifique, Paris (FR)

(*) Notice: Subject to any disclaimer, the term of this patent is extended or adjusted under 35 U.S.C. 154(b) by 0 days.

(21) Appl. No.: 09/546,250

(22) Filed: Apr. 10, 2000

Related U.S. Application Data

(60) Provisional application No. 60/128,511, filed on Apr. 9, 1999.

(51) Int. Cl.[7] .............................................. C07H 21/04
(52) U.S. Cl. .................... 536/24.3; 536/23.1; 435/91.1; 435/91.2
(58) Field of Search ............................ 536/24.3, 23.1; 435/91.2, 91.1

(56) References Cited

PUBLICATIONS

Fauron et al. Trends in Genetics, Jun. 1995, vol. 11, No. 6, pp. 228–235.*
Fauron and Havlik, (1989) "The maize mitochondrial genome of the normal type and the cytoplasmic male sterile type T have very different organization"; *Curr. Genet.* 15:149–154.
Isaac et al. (1985) "The maize cytochrome c oxidase subunit I gene: sequence, expression and rearrangement in cytoplasmic male sterile plants"; *EMBO Journal* 4(7):1617–1623.
Sangaré et al (1990) "Localization and organization of tRNA genes on the mitochondrial genomes of fertile and male–sterile lines of maize"; *Mol. Gen. Genet.* 223:224–232.

* cited by examiner

*Primary Examiner*—W. Gary Jones
*Assistant Examiner*—Juliet C. Einsmann
(74) *Attorney, Agent, or Firm*—Greenlee, Winner and Sullivan, P.C.

(57) ABSTRACT

A specific region of the maize mitochondrial genome has been found to have unique sequence in each of four different cytotypes: NA and NB (male fertile), S and C (male sterile). Specific primers allow PCR reactions to amplify, identify and measure each unique sequence. Using the method, said lots can be analyzed for contaminating cytotypes and unidentified cultivars can be typed.

8 Claims, 1 Drawing Sheet

US 6,346,612 B1

METHOD FOR IDENTIFYING DIFFERENT MAIZE CYTOTYPES AND FOR MEASURING THE CONTAMINATION OF MALE-FERTILE SEEDS MIXED WITH MALE-STERILE SEEDS

CROSS REFERENCE TO RELATED APPLICATIONS

This application claims priority from U.S. Provisional application No. 60/128,511 filed Apr. 9, 1999.

BACKGROUND OF THE INVENTION

Contamination of maize male-sterile seeds by male-fertile seeds can significantly reduce crop yields. Currently, such contamination can only be detected at the time of pollen maturation. It is then necessary to manually emasculate the maize plants resulting from this contamination. The process must be done within a short and specific time frame, within one week after pollen formation. The task is very expensive and labor-intensive. A typical cost ranges from 3,000 to 4,000 FF (french francs=US$600 to $800) per hectare. In France 60,000 hectares are used to provide sufficient maize seed for planting 3,000.000 hectares of maize production. The cost of production and land area required in the U.S. are proportionate. The price of hybrid seeds is about 20,000 FF (US$4,000) per hectare. This invention's practical application includes the use of a kit that will allow the PCR amplification of cytotype-specific mtDNA sequences.

SUMMARY OF THE INVENTION

One aspect of the invention concerns a polymerase chain reaction (PCR) method that allows one to distinguish and identify without any ambiguity, various male-fertile and male-sterile maize plants. This identification is based on the knowledge of sequences specific to the mitochondrial genome (mtDNA) of the various maize cytotypes. The method can be used to quantify contamination between the various cultivars. The invention also includes the specific sequences of maize mtDNA that have been found to be cytotype-specific.

A specific region in the maize mitochondrial genome has been shown to be rearranged through recombination in four different maize cytotypes: NA and NB (fertiles), S and C (steriles). PCR reactions allow the amplification of DNA fragments of different sizes which are specific to each cytotype. Unidentified cultivars can therefore be identified, and cross-contamination between cultivars quantified.

This invention can resolve two problems:

1) It will identify a maize cultivar cytoplasm whose source is questionable and may be subject to an ownership dispute.

2) It will identify and quantify contamination of fertile seeds within a set of sterile seeds. The quantification of contamination will allow one to estimate the eventual resulting decrease in crop yield so as to better control yields. Knowing how much contamination of fertile seeds is present within a set of male-sterile seeds is very important for seed companies since the beneficial effects of heterosis would be lost resulting in a significant decrease of crop yield. Furthermore certification and commercialization of maize seeds must meet specified quality control standards.

In general, the invention provides novel sequences of mtDNA which are specific for maize cytotypes NA, NB, S and C. Each of the disclosed mtDNA sequences contains one or more subsequences which are unique for the designated cytotype. A method is provided using PCR amplification of the cytotype-specific subsequences to identify the cytotype of a given sample of maize tissue, seed or flour. Further, the method makes it possible to identify the cytotype composition of a sample of mixed cytotypes, for example in seeds or flour. Certain primer sequences for amplifying cytotype specific subsequences are exemplified herein. One skilled in the art will recognize that other primers can be chosen, based upon the disclosed mtDNA sequences, and the detailed conditions for DNA extraction, amplification, and analysis can all be varied within parameters known to those skilled in the art, as may be desired or necessary, depending on the particular needs of those using the method. All such variations will be understood as falling within the scope of the invention.

DETAILED DESCRIPTION OF THE INVENTION

Figure 1:
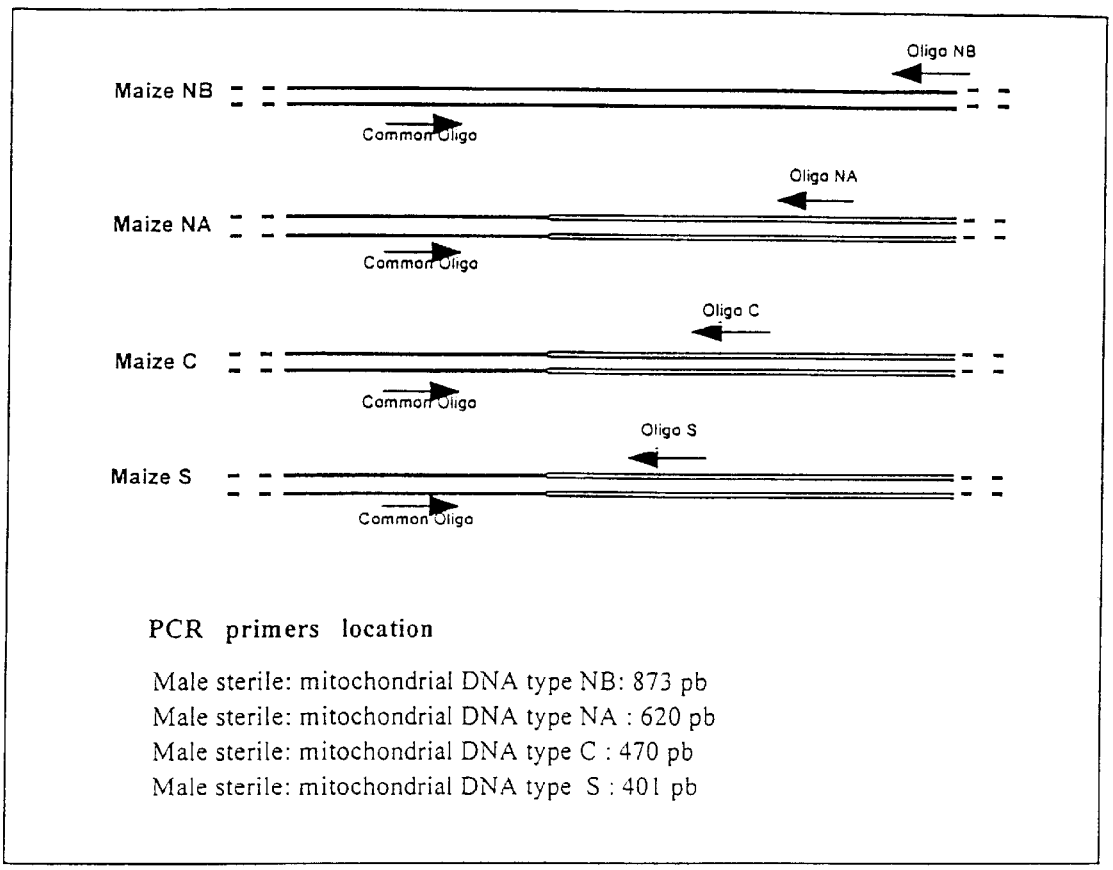
FIG. 1 is a diagram showing the relative location of primers employed for PCR identification of maize cytotypes NA, NB, S and C. Sequences of the designated primers is given in Table 1.

Total DNA Extraction (Using a Sample of 1,000 Kernels) From Maize Seeds

Maize kernels were allowed to germinate in the dark at 25° C. for 5 to 7 days. The etiolated small plants were then collected and homogenized in a Waring Blendor with the extraction buffer [$CH_3COONa$ (sodium acetate) 100 mM pH=4.8; EDTA (disodium ethylenediamine tetra-acetate) 50 mM pH=8; NaCl 500 mM; PVP (Polyvinylpyrrolidone PM 10000) 2%; Cystein 60 mM]. SDS (sodium dodecyl sulfate) was added to the homogenate to a final concentration of 1%. Denaturation was allowed for 10 mn at 65° C. and the lysate centrifuged at 10,000 g for 10 min at room temperature. The proteins were precipitated in presence of ⅓ volume of potassium γM and the mixture incubated for 20 mn at 0° C. Precipitated proteins were eliminated by centrifugation at 10,000 g for 10 mn at 4° C. A DEAE-cellulose (Diethylaminoethyl-cellulose) suspension (¼ V) was added to the DNA-containing supernatant. DEAE-cellulose (DE 52 Whatman) was prepared in the elution buffer (NaCl 2M; Tris-HCl 10 mM pH=7.5; EDTA 1 mM) then resuspended in the wash buffer (NaCl 400 mM; Tris-HCl 10 mM pH=7.5; EDTA 1 mM). The mixture was decanted, the supernatant poured off gently and the matrix washed twice with the wash buffer to eliminate proteins, polysaccharides and metabolites not bound to the matrix. The nucleic acids were eluted with the elution buffer and precipitated with 2.5 volumes of absolute ethanol and 0.5 volume of ammonium acetate 7.5M for 30 mn at −20° C. The precipitate was centrifuged for 15 mn at 15,000 g at 4° C. and resuspended in water or TE (Tris-EDTA) 0.1 mM. RNA was eliminated with RNAse A: 50 μl (10 mg/ml) in 100 μl of DNA mixture for 30 mn at 37° C. DNA was isolated by another phenol/chloroform extraction and ethanol precipitation. The DNA pellet was resuspended in 500 μl water or TE (Tris-EDTA) 0.1 mM and quantified by readings at OD260 and agarose gel electrophoresis.

From Maize Flour

We offer an alternative method of DNA extraction in order to overcome two possible technical problems concerning space and time: to eliminate the need of space to germinate the seeds and to eliminate the five days needed to grow the seedlings.

The 1,000 maize seeds were ground in a mill in order to obtain a fine flour. The extraction buffer was made of Tris-HCl 200 mM pH=8.0; EDTA 70 mM; NaCl 2M. 0.5 g. of sodium bisulfite was added to 100 ml of buffer just before use. After adding SDS at 1% final concentration, the mixture was gently homogenized and incubated at 65° C. for one hour (gently vortex every 10 min). The homogenate was centrifuged at 16,000 g for 15 min at 4° C. The supernatant was used for DNA precipitation with 1 volume isopropanol. The pellet was dried out in the speedvac and resuspended in 500 µl water and mixed with an equal volume of phenol/chloroform/isoamyl alcohol (10/10/1 v/v). After a 10 min centrifugation at 13,000 g at room temperature, the upper layer was saved and 500 µl of chloroform is added; the mixture was vortexed and centrifuged for 10 mn at 13,000 g at room temperature. The upper phase was once more saved for DNA precipitation using 1/10 volume sodium acetate 3M and 1 volume of isopropanol. After 15 mn at 4° C. followed by a 15 mn centrifugation at 13,000 at 4° C., the DNA pellet was washed with 70% ethanol and dried. This final DNA pellet was resuspended into 100 µl of nanopure water and the OD was taken at 260 nm.

The Amplification of the Various Maize Cytotypes mtDNA Sequences

Plasmid Clones Containing the Sequences Specific to Each Cytoplasm

The DNA sequences from four clones containing mtDNA BamH1 fragments derived from the four maize cytotypes: NA, NB, C, S have been determined. Comparison of these sequences show that each DNA fragment contains a common sequence of variable length followed by a sequence unique to each cytotype (see below).

SEQ ID NO:1=Maize sterile cytotype S mtDNA
SEQ ID NO:2=Maize sterile cytotype C mtDNA
SEQ ID NO:3=Maize fertile cytotype NA mtDNA
SEQ ID NO:4=Maize fertile cytotype NB mtDNA

```
The sequences
        1                                                                  50
     S  CGACTCACTA TAGGGAATTC GAGCTCGGTA CCCGGGGATC CCCCCCGCAT
     C  CGACTCACTA TAGGGAATTC GAGCTCGGTA CCCGGGGATC CCCCCCGCAT
    NA  CGACTCACTA TAGGGAATTC GAGCTCGGTA CCCGGGGATC CCCCCCGCAT
    NB  CGACTCACTA TAGGGAATTC GAGCTCGGTA CCCGGGGATC CCCCCCGCAT 51                                                                 100
     S  TCTGATCAGG TTCGTTACCC ATTCCGCTGT GGTCATCAAA GAAGAATAAT
     C  TCTGATCAGG TTCGTTACCC ATTCCGCTGT GGTCATCAAA GAAGAATAAT
    NA  TCTGATCAGG TTCGTTACCC ATTCCGCTGT GGTCATCAAA GAAGAATAAT
    NB  TCTGATCAGG TTCGTTACCC ATTCCGCTGT GGTCATCAAA GAAGAATAAT 101                                                                 150
     S  AAAAAAGTGC TGTTGTTACA CTCAACAGAG TGAAAACGCG AGCAGCCCAA
     C  AAAAAAGTGC TGTTGTTACA CTCAACAGAG TGAAAACGCG AGCAGCCCAA
    NA  AAAAAAGTGC TGTTGTTACA CTCAACAGAG TGAAAACGCG AGCAGCCCAA
    NB  AAAAAAGTGC TGTTGTTACA CTCAACAGAG TGAAAACGCG AGCAGCCCAA 151                                                                 200
     S  ACTGGGCAAC GCGGCCATAA AGCGCGAACC AACATCCGTG ATACGAAAAC
     C  ACTGGGCAAC GCGGCCATAA AGCGCGAACC AA6ATCCGTG ATACGAAAAC
    NA  ACTGGGCAAC GCGGCCATAA AGCGCGAACC AACATCCGTG ATACGAAAAC
    NB  ACTGGGCAAC GCGGCCATAA AGCGCGAACC AACATCCGTG ATACGAAAAC 201                                                                 250
     S  CAAAATCAGA ATGAGGAAGA AAAGGATATC TTTAGGTAAG TCATGAAAAT
     C  CAAAATCAGA ATGAGGAAGA AAAGGATATC TTTAGGTAAG TCATGAAAAT
    NA  CAAAATCAGA ATGAGGAAGA AAAGGATATC TTTAGGTAAG TCATGAAAAT
    NB  CAAAATCAGA ATGAGGAAGA AAAGGATATC TTTAGGTAAG TCATGAAAAT 251                                                                 300
     S  GAAAACCCAA TAAGAACTTA CCCAATAATT TAGAACAGAT CACTTCCAAA
     C  GAAAACCCAA TAAGAACTTA CCCAATAATT TAGAACAGAT CACTTCCAAA
    NA  GAAAACCCAA TAAGAACTTA CCCAATAATT TAGAACAGAT CACTTCCAAA
    NB  GAAAACCCAA TAAGAACTTA CCCAATAATT TAGAACAGAT CACTTCCAAA 301                                                                 350
     S  CGAGACATGA TGAGCTAAAG TCAAAATAAA ATGCAAGAGA AATTCAAATT
     C  CGAGACATGA TGAGCTAAAG TCAAAATAAA ATGCAAGAGA AATTCAAATT
    NA  CGAGACATGA TGAGCTAAAG TCAAAATAAA ATGCAAGAGA AATTCAAATT
    NB  CGAGACATGA TGAGCTAAAG TCAAAATAAA ATGCAAGAGA AATTCAAATT 351                                                                 400
     S  ATGTAAGGCT TAGAAAAAAG TCCTGCGTAG AGTCCACGGG GAGCCTTTTT
     C  ATGTAAGGCT TAGAAAAAAG TCCTGCGTAG AGTCCACGGG GAGCCTTTTT
    NA  ATGTAAGGCT TAGAAAAAAG TCCTGCGTAG AGTCCACGGG GAGCCTTTTT
    NB  ATGTAAGGCT TAGAAAAAAG TCCTGCGTAG AGTCCACGGG GAGCCTTTTT 401                                                                 450
     S  CGATTTGATC TCTAGTCAAA CTAAGACTGG AGCTTGAAGC CACTACTCTA
     C  CGATTTGATC TCTAGTCAAA CTAAGACTGG AGCTTGAAGC CACTACTCTA
    NA  CGATTTGATC TCTAGTCAAA CTAAGACTGG AGCTTGAAGC CACTACTCTA
    NB  CGATTTGATC TCTAGTCAAA CTAAGACTGG AGCTTGAAGC CACTACTCTA 451                                                                 500
```

```
                      -continued
   S  GAACCGGAAG AAGCCTAACT TCTGCATTTT GAGTAGATTT TCTGACTATC
   C  GAACCGGAAG AAGCCTAACT TCTGCATTTT GAGTAGATTT TCTGACTATC
   NA GAACCGGAAG AAGCCTAACT TCTGCATTTT GAGTAGATTT TCTGACTATC
   NB GAACCGGAAG AAGCCTAACT TCTGCATTTT GAGTAGATTT TCTGACTATC 501                      * common oligo direct   550
   S  ATTTGCCTTG AATTACAATA CGATAAATCTT CGATTGGTAG AAGTGAGTCC
   C  ATTTGCCTTG AATTACAATA CGATAAATCTT CGATTGGTAG AAGTGAGTCC
   NA ATTTGCCTTG AATTACAATA CGATAAATCTT CGATTGGTAG AAGTGAGTCC
   NB ATTTGCCTTG AATTACAATA CGATAAATCTT CGATTGGTAG AAGTGAGTCC 551*                                             600
   S  GGATCTCCCT CTTTTCCACT AAACCCGCCA CTCCTACTTG TACTTTATTT
   C  GGATCTCCCT CTTTTCCACT AAACCCGCCA CTCCTACTTG TACTTTATTT
   NA GGATCTCCCT CTTTTCCACT AAACCCGCCA CTCCTACTTG TACTTTATTT
   NB GGATCTCCCT CTTTTCCACT AAACCCGCCA CTCCTACTTG TACTTTATTT 601                                              650
   S  TCCACCTGGC TAGCTTCAAT TGCTTAGTAG GGAGTTTCCA TCCTTGACTT
   C  TCCACCTGGC TAGCTTCAAT TGCTTAGTAG GGAGTTTCCA TCCTTGACTT
   NA TCCACCTGGC TAGCTTCAAT TGCTTAGTAG GGAGTTTCCA TCCTTGACTT
   NB TCCACCTGGC TAGCTTCAAT TGCTTAGTAG GGAGTTTCCA TCCTTGACTT 651                                              700
   S  TCGCGGTTCT TTCTTTGCTT TCTTCAGTTG TGTTGAGGAG CTATCTTTTG
   C  TCGCGGTTCT TTCTTTGCTT TCTTCAGTTG TGTTGAGGAG CTATCTTTTG
   NA TCGCGGTTCT TTCTTTGCTT TCTTCAGTTG TGTTGAGGAG CTATCTTTTG
   NB TCGCGGTTCT TTCTTTGCTT TCTTCAGTTG TGTTGAGGAG CTATCTTTTG 701                                              750
   S  AACCCAACTA ACTCTTAAAT CCGAACTTTC CCTTGCTTAC GCCCCTAGAA
   C  AACCCAACTA ACTCTTAAAT CCGAACTTTC CCTGCAGCTT TAGGGCTTCT
   NA AACCCAACTA ACTCTTAAAT CCGAACTTTC CCTGCAGCTT TAGGGCTTCT
   NB AACCCAACTA ACTCTTAAAT CCGAACTTTC CCTGCAGCTT TAGGGCTTCT
                      End of common for S *

751                                              800
   S  ACTCCGTGAA AAAACCACCT CGTTTTTCCA TAAATAAAGG ATTCCTAATA
   C  AGTGAGGAGA GGTGATCTCT AGTTTCTCAT TCCGATAGCC ATCTCGATTA
   NA AGTGAGGAGA GGTGATCTCT AGTTTCTCAT TCCGATAGCC ATCTCGATTA
   NB AGTGAGGAGA GGTGATCTCT AGTTTCTCAT TCCGATAGCC ATCTCGATTA 801                                              850
   S  AAGTTTTTAC ATATCATATC CCAGCGGTAT TTTTATAATA ATTTTTGCAT
   C  ACTGAGTTGA CTTGTGAGCT CCCCTAACCC GGCAGGCAGG CCAAAGAATG
   NA ACTGAGTTGA CTTGTGAGCT CCCCTAACCC GGCAGGCAGG CCAAAGAATG
   NB ACTGAGTTGA CTTGTGAGCT CCCCTAACCC GGCAGGCAGG CCAAAGAATG 851                                              900
   S  AAATAAAGTA TAATTTCCAC AAAATAACAC TTTTAGGCGC CCACTTGAAA
   C  AAGGGCAGTG AAAATGGTTT CTTCTTCTGG CTAATTCCGA TACGAATACC
   NA AAGGGCAGTG AAAATGGTTT CTTCTTCTGG CTAATTCCGA TACGAATACC
   NB AAGGGCAGTG AAAATGGTTT CTTCTTCTGG CTAATTCCGA TACGAATACC

* oligo S reverse           *                 950
   S  TTCAACTTAA CGTTGGACCT TGACCAGGCC CTCTCTATTT CCAGAATT
   C  AAAAACAGCT TACTTCCGTT CGTGTCCTCG GAAATTGCAA TTCATTCACA
   NA AAAAACAGCT TACTTCCGTT CGTGTCCTCG GAAATTGGAT TACTTATGAG
   NB AAAAACAGCT TACTTCCGTT CGTGTCCTCG GAAATTGGAT TACTTATGAG
                          End of common for C *

951               *   oligo c reverse          *1000
   C  TCTGCTCCTA TCTATTCTAT GCTTGCTTAC CAATCGGGAC TTGCAATTCC
   NA TTTCTTCGGT GCAAAAGTAG GCAAGTCCAT TTTCTCGTGT TTTTCGTCCT
   NB TTTCTTCGGT GCAAAAGTAG GCAAGTCCAT TTTATCGTGT TTTTCGTCCT 1001                                             1050
   C  TATCACCCGC CGGAGGCAGA TTACTTAATC TGAAAGCGTT ATTTCACATT
   NA CAAGACCTGA TTTTCCAAAG AGCATTTCAT ATAGCTGCAA AAGTTGCTCA
   NB CAAGACCTGA TTTTCCAAAG AAAATAGCCT GCCAAAGAGC TAGCTATAGA
                          * end of common between NA and NB 1051                                             1100
   C  CGTTATTTCA TATCATATGA ATTAGGCGGA TCATACACCG ATCTCAGAAC
   NA TCCGATTTTC CCTCGCTTTT ATTCGTAACA TGGCGTAGTT ACTCATTGGG
   NB AATACAGTCA GTCGGGGTAA ACTGAAAGAA GGAAATCTAC ATTCATAGAT 1101               * oligo NA reverse          *1150
   C  TAATACGCTT TCGCTTTCTC CTGACCCTCA ATCCAAAAGA AAAGGTTTGG
   NA TCCGCTGAGA AGAAAACAAT AGGTCGTCAC TACCTATGCT TTCATCTAGA
```

```
                                              -continued
NB AGTAGGGCAA TAGGCTCACT TACATAGTGG GGACAGCAAT AGGCTCACTT 1151                                              1200
 C CGTTGCAGTT CATATGCTTC CTTGCGCTAG AAACCAATAC GCACGTACGA
NA GGAAGTCAGG CTGTGATTCG TAACATGGCG TAGTTACTCA CAGGCCGTGG
NB ACTTTTGAAA TAAGAGGGTC GGTCAACTCT CGGCAGATAG GGTAGTTGCT 1201                                              1250
 C GGCCTACGAT TCTCTAGTTG TATTGGCAAG GGAAAGAAGA TGCTATGGGA
NA ATCTCCTTTT TCTAATCAAG CAGCAGGCCG TGGGTTTTCT GGTTCTGCGC
NB AAATAAAAGC AAAGAAAGAG TGAGTTGAAA GAAGAAATGT ATGTGGGTCA 1251                                              1300
 C ATGTTTGGAA TGAAA
NA TTCAGAAGAG GAAAGTTTCC GTGATTCGTA TCTGCTTTGA GGGCAGGTC
NB CCATATAATA TATATAATAG TACCTAACTT ACTAGGTATC TCGGTCAACT 1301                                              1350
NB GCTAGCTTTT CATCCTTGGT GCAGTATTTC CACCTTCTAT TGCTTTGCTT 1351                    * oligo NB reverse       *1400
NB GCCTAGCTCT TACTACCGTT ATTTCCATCT GAGAACTAGA CGCCCGGTTC 1401                                              1450
NB AACTTAGCCA AGTTAAGGGA ACGCACTACT CTTCCCTACA AGCAACGGAT 1451                                              1500
NB TGAGGCTAGC GCGAAAGCCG GTGCGCGTTA GGCGCATCCG TTTTCTTGCT 1501                                              1550
NB TAGTAGTTAC TCACTGGGAT TCCCGCAGTG CAGCCGTTGC TTGTTGGGCT 1551                                              1600
NB ACAAAGCACT TCTTAGACGG AAGAGCGGCA AGCAAGCCTA CTCAAGTACC 1601                                              1650
NB TAGCACTCCA CAACCCATTA GTTGGAAGGC AATCAGCAAC TTAGCACACT 1651                                              1700
NB AGAGCATACA ACGACCTTTA GCAACCTTTT CTCGAGCGAT AGTCTAGTAG 1701                                              1750
NB GTCAAGCCCG AGTGGAGGCC ATCCATCCCT TTCTGATGAA ACCTTTGTTG 1751                1794
NB CCCTAGCTTG AATTGAAGGT TTGGCTAAGG ATGGGATCC TCTA
```

The Polymerase Chain Reactions

In order to amplify the DNA, we have synthesized five oligonucleotides: one which hybridizes to the DNA sequence common to the four fragments and four others, each one specific to the unique sequence of each of the four cytotypes: NA, NB, C, S.

Choice of Primers

These five synthetic oligonucleotides have been chosen so that they allow amplification in the same experimental conditions for all reactions. The denaturation temperature is high enough to permit full hybridization at 55° C. (see below). To insure a better annealing, the last 3' chosen as a C or a G.

TABLE 1

Sequences of the primers

| Oligo | Sequence | O | P | SEQ ID NO. |
|---|---|---|---|---|
| OLIGO-NA | GATGAAAGCA TAGGTAGTGA CGACC | R | 1122–1146 | 5 |
| OLIGO-NB | AACCQGGCGT CTAGTTCTCA GATGG | R | 1375–1399 | 6 |
| OLIGO-S | CTGGTCAAGG TCCAACGTTA AGTTG | R | 904–927 | 7 |
| OLIGO-C | TTGCAAGTCC CGATTGGTAA GCAAGC | R | 971–996 | 8 |
| OLIGO-com | ATCTTCGATT GGTAGAAGTG AGTCCG | D | 526–551 | 9 |

The sequences of these oligonucleotides are as follow:
O = Orientation  [D = direct; R - reverse]
P = Position    [base pair number from the above sequence]

Experimental Procedure a) To find if a set of sterile seeds are contaminated with one or both the fertile cytotypes, the following reaction was set up.

The reactions were done in a final volume of 50 μl
200 ng DNA
5 μl NTP 2 mM
5 μl enzyme buffer
0.5 μl AmpliTaq polymerase (2.5 U)
4 μl MgCl$_2$ 20 mM 4 µl oligo com.

4 µl oligo NA

4 µl oligo NB

4 µl DNA @ 50 ng/µl 19.5 µl H$_2$O

The PCR cycles

Denaturation: 1 mn 95° C.

Amplification: 40 sec. at 95° C.; 40 sec. at 55° C.; 40 sec. at 72° C.

30 cycles of amplification b) Results

The amplification products were visualized on a 1.2% agarose gel stained with ethidium bromide. The size of the DNA fragments flanked by the 2 oligonucleotides were: fertile maize type NB: 873 bp; fertile maize type NA: 620 bp; male sterile maize type C: 470 bp; male sterile type S: 401 bp. A single PCR was enough to identify the presence of fertile maize contamination within a male-sterile sample.

Application of this method using total DNA extracted from maize seedlings or flour has shown that it is possible to characterize each maize cytotype in a mixture of cytotypes without any ambiguity. Some experiments have been done by mixing decreasing amount of DNA from one cytotype with the other cytotypes which have shown that it is possible to detect the specific fragment without any ambiguity, in a ratio 1 to 10,000. This corresponds to a contamination of one seed among 10,000 seeds. This ratio can be substantially lowered by optimizing the PCR method. The method was also applied in a real environment with mixed maize seeds from which the amount of contamination was determined. Quantification of the contamination was assessed by recording the number of PCR cycles needed to obtain the same amount of DNA amplified with different amount of DNA, then extrapolating to the origin (PCR cycle number=0). Therefore this invention allows the identification of the four maize cytotypes, and the quantification of each cytotype within a mixture.

c) Control Reactions

1) To avoid amplification of foreign DNA traces that might be present in the buffers, the same PCR reactions must be conducted without DNA extracted from the maize kernels.

2) Control of DNA synthesis. If the PCR test is negative, one must be sure that non-amplification is real and not the result of a faulty synthesis. The same PCR reactions must be done in the presence of sterile-specific oligos in order to assure that the polymerase is working.

Today's methods do not allow one to identify in a precise manner the different maize cytotypes. The identification is obtained by performing crosses that require more than one generation. The identification is therefore time consuming, tedious and costly. The method of the invention is molecular-based PCR method leading to a quick and precise result. The method also allows one to quantify the amount of each cytotype in a mixture, which is not possible by doing traditional crosses.

Time needed to realize those tests is two days from the time the raw material (flour or seedlings) is available. It takes one week if the maize kernels need to be germinated in the dark.

BIBLIOGRAPHY a) Fauron, C. M. R. and Havlik, M., The maize mitochondrial genome of the normal type and the cytoplasmic male sterile type T have very different organization, *Curr. Genet.*, 15, 149, 1989.

b) Sangaré, A., Weil, J. H., Grienenberger, J. M., Fauron, C. and Lonsdale, D., Localization and organization of tRNA genes on the mitochondrial genomes of fertile and male-sterile lines of maize, *Mol. Gen. Genet.*, 223, 224, 1990.

We claim:

1. A primer pair which amplifies a sequence of maize mtDNA specific for a maize cytotype selected from the group NA, NB, S or C, in a polymerase chain reaction wherein said primer pair has primers that comprise 25 contiguous nucleic acids from the nucleotide sequences shown in SEQ ID NOs: 1–4.

2. The primer pair of claim 1 wherein the maize cytotype is NA, the primers comprising the sequences of SEQ ID NO:9 and SEQ ID NO:5.

3. The primer pair of claim 1 wherein the maize cytotype is NB, the primers comprising the sequences of SEQ ID NO:9 and SEQ ID NO:6.

4. The primer pair of claim 1 wherein the maize cytotype is S, the primers comprising the sequences of SEQ ID NO:9 and SEQ ID NO:7.

5. The primer pair of claim 1 wherein the maize cytotype is C, the primers comprising the sequences of SEQ ID NO:9 and SEQ ID NO:8.

6. The primer pair of claim 1 wherein the maize mtDNA specific for cytotype NA has the sequence of SEQ ID NO:3, the mtDNA specific for cytotype NB has the sequence of SEQ ID NO:4, the mtDNA specific for cytotype S has the sequence of SEQ ID NO:1 and the mtDNA specific for cytotype C has the sequence of SEQ ID NO:2.

7. A kit for identifying and measuring the cytotypes present in a sample of maize seeds or maize flour comprising five oligonucleotides having the sequences of SEQ ID NOS.5–9 in amounts suitable for amplifying specific segments of maize mtDNA, using a polymerase chain reaction.

8. The kit of claim 7 wherein the oligonucleotides are prepackaged pairwise, the pairs being SEQ ID NO:9 with SEQ ID NO:5, SEQ ID NO: 9 with SEQ ID NO:6; SEQ ID NO:9 with SEQ ID NO:7, and SEQ ID NO:9 with SEQ ID NO:8.

* * * * *

UNITED STATES PATENT AND TRADEMARK OFFICE
CERTIFICATE OF CORRECTION

PATENT NO.   : 6,346,612 B1
DATED        : February 12, 2002
INVENTOR(S)  : Fauron and Grienenberger Page 1 of 1

It is certified that error appears in the above-identified patent and that said Letters Patent is hereby corrected as shown below:

<u>Column 2,</u>
Line 37, please replace "potassium γM" with -- potassium 5M --.

<u>Column 7,</u>
Table 1, the sequence for oligonucleotide primer, "OLIGO-NB", please replace "AACCQGGCGT CTAGTTCTCA GATGG" with -- AACCGGGCGT CTAGTTCTCA GATGG --.

Signed and Sealed this

Fifteenth Day of October, 2002

*Attest:*

JAMES E. ROGAN
*Attesting Officer*    *Director of the United States Patent and Trademark Office*

SEQUENCE LISTING

<160> NUMBER OF SEQ ID NOS: 9

<210> SEQ ID NO 1
<211> LENGTH: 948
<212> TYPE: DNA
<213> ORGANISM: Maize

<400> SEQUENCE: 1

```
cgactcacta tagggaattc gagctcggta cccggggatc cccccgcat  tctgatcagg      60 ttcgttaccc attccgctgt ggtcatcaaa gaagaataat aaaaaagtgc tgttgttaca     120
ctcaacagag tgaaaacgcg agcagcccaa actgggcaac gcggccataa agcgcgaacc     180
aacatccgtg atacgaaaac caaaatcaga atgaggaaga aaaggatatc tttaggtaag     240
tcatgaaaat gaaaacccaa taagaactta cccaataatt tagaacagat cacttccaaa     300
cgagacatga tgagctaaag tcaaaataaa atgcaagaga aattcaaatt atgtaaggct     360
tagaaaaaag tcctgcgtag agtccacggg gagccttttt cgatttgatc tctagtcaaa     420
ctaagactgg agcttgaagc cactactcta gaaccggaag aagcctaact tctgcatttt     480
gagtagattt tctgactatc atttgccttg aattacaata cgataatctt cgattggtag     540
aagtgagtcc ggatctccct cttttccact aaacccgcca ctcctacttg tactttattt     600
```

```
tccacctggc tagcttcaat tgcttagtag ggagtttcca tccttgactt tcgcggttct    660
ttctttgctt tcttcagttg tgttgaggag ctatcttttg aacccaacta actcttaaat    720
ccgaactttc ccttgcttac gcccctagaa actccgtgaa aaaccacct cgttttcca     780 taaataaagg attcctaata aagttttac atatcatatc ccagcggtat ttttataata    840 attttttgcat aaataaagta taatttccac aaaataacac ttttaggcgc ccacttgaaa   900
ttcaacttaa cgttggacct tgaccaggcc ctctctattt ccagaatt                948
```

```
<210> SEQ ID NO 2
<211> LENGTH: 1265
<212> TYPE: DNA
<213> ORGANISM: Maize

<400> SEQUENCE: 2
cgactcacta tagggaattc gagctcggta cccggggatc cccccgcat tctgatcagg     60 ttcgttaccc attccgctgt ggtcatcaaa gaagaataat aaaaaagtgc tgttgttaca   120
ctcaacagag tgaaaacgcg agcagcccaa actgggcaac gcggccataa agcgcgaacc   180
aacatccgtg atacgaaaac caaaatcaga atgaggaaga aaggatatc tttaggtaag    240 tcatgaaaat gaaacccaa taagaactta cccaataatt tagaacagat cacttccaaa    300
cgagacatga tgagctaaag tcaaaataaa atgcaagaga aattcaaatt atgtaaggct   360
tagaaaaaag tcctgcgtag agtccacggg gagccttttt cgatttgatc tctagtcaaa   420
ctaagactgg agcttgaagc cactactcta gaaccggaag aagcctaact tctgcatttt   480
gagtagattt tctgactatc atttgccttg aattacaata cgataatctt cgattggtag   540
aagtgagtcc ggatctccct cttttccact aaacccgcca ctcctacttg tactttattt   600
tccacctggc tagcttcaat tgcttagtag ggagtttcca tccttgactt tcgcggttct   660
ttctttgctt tcttcagttg tgttgaggag ctatcttttg aacccaacta actcttaaat   720
ccgaactttc cctgcagctt tagggcttct agtgaggaga ggtgatctct agtttctcat   780
tccgatagcc atctcgatta actgagttga cttgtgagct cccctaaccc ggcaggcagg   840
ccaaagaatg aagggcagtg aaaatggttt cttcttctgg ctaattccga tacgaatacc   900
aaaaacagct tacttccgtt cgtgtcctcg gaaattgcaa ttcattcaca tctgctccta   960
tctattctat gcttgcttac caatcgggac ttgcaattcc tatcacccgc cggaggcaga  1020
ttacttaatc tgaaagcgtt atttcacatt cgttatttca tatcatatga attaggcgga  1080
tcatacaccg atctcagaac taatacgctt tcgctttctc ctgaccctca atccaaaaga  1140
aaaggttggg cgttgcagtt catatgcttc cttgcgctag aaaccaatac gcacgtacga  1200
ggcctacgat tctctagttg tattggcaag ggaaagaaga tgctatggga atgtttggaa  1260
tgaaa                                                              1265
```

```
<210> SEQ ID NO 3
<211> LENGTH: 1299
<212> TYPE: DNA
<213> ORGANISM: Maize

<400> SEQUENCE: 3
cgactcacta tagggaattc gagctcggta cccggggatc cccccgcat tctgatcagg     60 ttcgttaccc attccgctgt ggtcatcaaa gaagaataat aaaaaagtgc tgttgttaca   120
ctcaacagag tgaaaacgcg agcagcccaa actgggcaac gcggccataa agcgcgaacc   180
aacatccgtg atacgaaaac caaaatcaga atgaggaaga aaggatatc tttaggtaag    240
```

-continued

```
tcatgaaaat gaaaacccaa taagaactta cccaataatt tagaacagat cacttccaaa    300
cgagacatga tgagctaaag tcaaaataaa atgcaagaga aattcaaatt atgtaaggct    360
tagaaaaaag tcctgcgtag agtccacggg gagccttttt cgatttgatc tctagtcaaa   420
ctaagactgg agcttgaagc cactactcta gaaccggaag aagcctaact tctgcatttt    480
gagtagattt tctgactatc atttgccttg aattacaata cgataatctt cgattggtag    540
aagtgagtcc ggatctccct cttttccact aaacccgcca ctcctacttg tactttattt    600
tccacctggc tagcttcaat tgcttagtag ggagtttcca tccttgactt tcgcggttct   660
ttctttgctt tcttcagttg tgttgaggag ctatcttttg aacccaacta actcttaaat    720
ccgaactttc cctgcagctt tagggcttct agtgaggaga ggtgatctct agtttctcat   780
tccgatagcc atctcgatta actgagttga cttgtgagct cccctaaccc ggcaggcagg    840
ccaaagaatg aagggcagtg aaaatggttt cttcttctgg ctaattccga tacgaatacc    900
aaaaacagct tacttccgtt cgtgtcctcg gaaattggat tacttatgag tttcttcggt    960
gcaaaagtag gcaagtccat ttctcgtgt ttttcgtcct caagacctga ttttccaaag   1020
agcatttcat atagctgcaa aagttgctca tccgattttc cctcgctttt attcgtaaca    1080
tggcgtagtt actcattggg tccgctgaga agaaaacaat aggtcgtcac tacctatgct    1140
ttcatctaga ggaagtcagg ctgtgattcg taacatggcg tagttactca caggccgtgg    1200
atctcctttt tctaatcaag cagcaggccg tgggttttct ggttctgcgc ttcagaagag    1260
gaaagtttcc gtgattcgta tctgctttga gggcaggtc                          1299
```

<210> SEQ ID NO 4
<211> LENGTH: 1794
<212> TYPE: DNA
<213> ORGANISM: Maize

<400> SEQUENCE: 4

```
cgactcacta tagggaattc gagctcggta cccggggatc ccccccgcat tctgatcagg    60
ttcgttaccc attccgctgt ggtcatcaaa gaagaataat aaaaaagtgc tgttgttaca    120
ctcaacagag tgaaaacgcg agcagcccaa actgggcaac gcggccataa agcgcgaacc    180
aacatccgtg atacgaaaac caaaatcaga atgaggaaga aaaggatatc tttaggtaag    240
tcatgaaaat gaaaacccaa taagaactta cccaataatt tagaacagat cacttccaaa    300
cgagacatga tgagctaaag tcaaaataaa atgcaagaga aattcaaatt atgtaaggct    360
tagaaaaaag tcctgcgtag agtccacggg gagccttttt cgatttgatc tctagtcaaa   420
ctaagactgg agcttgaagc cactactcta gaaccggaag aagcctaact tctgcatttt    480
gagtagattt tctgactatc atttgccttg aattacaata cgataatctt cgattggtag    540
aagtgagtcc ggatctccct cttttccact aaacccgcca ctcctacttg tactttattt    600
tccacctggc tagcttcaat tgcttagtag ggagtttcca tccttgactt tcgcggttct   660
ttctttgctt tcttcagttg tgttgaggag ctatcttttg aacccaacta actcttaaat    720
ccgaactttc cctgcagctt tagggcttct agtgaggaga ggtgatctct agtttctcat   780
tccgatagcc atctcgatta actgagttga cttgtgagct cccctaaccc ggcaggcagg    840
ccaaagaatg aagggcagtg aaaatggttt cttcttctgg ctaattccga tacgaatacc    900
aaaaacagct tacttccgtt cgtgtcctcg gaaattggat tacttatgag tttcttcggt    960
gcaaaagtag gcaagtccat tttatcgtgt ttttcgtcct caagacctga ttttccaaag   1020
```

-continued

```
aaaatagcct gccaaagagc tagctataga aatacagtca gtcggggtaa actgaaagaa    1080
ggaaatctac attcatagat agtagggcaa taggctcact tacatagtgg ggacagcaat    1140
aggctcactt acttttgaaa taagagggtc ggtcaactct cggcagatag ggtagttgct    1200
aaataaaagc aaagaaagag tgagttgaaa gaagaaatgt atgtgggtca ccatataata    1260
tatataatag tacctaactt actaggtatc tcggtcaact gctagctttt catccttggt    1320
gcagtatttc caccttctat tgctttgctt gcctagctct tactaccgtt atttccatct    1380
gagaactaga cgcccggttc aacttagcca agttaaggga acgcactact cttccctaca    1440
agcaacggat tgaggctagc gcgaaagccg gtgcgcgtta ggcgcatccg ttttcttgct    1500
tagtagttac tcactgggat tcccgcagtg cagccgttgc ttgttgggct acaaagcact    1560
tcttagacgg aagagcggca agcaagccta ctcaagtacc tagcactcca aacccatta    1620 gttggaaggc aatcagcaac ttagcacact agagcataca acgaccttta gcaacctttt    1680
ctcgagcgat agtctagtag gtcaagcccg agtggaggcc atccatccct ttctgatgaa    1740
acctttgttg ccctagcttg aattgaaggt ttggctaagg atgggatcc tcta           1794
```

<210> SEQ ID NO 5
<211> LENGTH: 25
<212> TYPE: DNA
<213> ORGANISM: Maize
<220> FEATURE:
<221> NAME/KEY: misc_feature
<222> LOCATION: (1)..(25)
<223> OTHER INFORMATION: Oligonucleotide primer

<400> SEQUENCE: 5
gatgaaagca taggtagtga cgacc                                          25

<210> SEQ ID NO 6
<211> LENGTH: 25
<212> TYPE: DNA
<213> ORGANISM: Maize
<220> FEATURE:
<221> NAME/KEY: misc_feature
<222> LOCATION: (1)..(25)
<223> OTHER INFORMATION: Oligonucleotide primer

<400> SEQUENCE: 6
aaccgggcgt ctagttctca gatgg                                          25

<210> SEQ ID NO 7
<211> LENGTH: 25
<212> TYPE: DNA
<213> ORGANISM: Maize
<220> FEATURE:
<221> NAME/KEY: misc_feature
<222> LOCATION: (1)..(25)
<223> OTHER INFORMATION: Oligonucleotide primer

<400> SEQUENCE: 7
ctggtcaagg tccaacgtta agttg                                          25

<210> SEQ ID NO 8
<211> LENGTH: 26
<212> TYPE: DNA
<213> ORGANISM: Maize
<220> FEATURE:
<221> NAME/KEY: misc_feature
<222> LOCATION: (1)..(26)
<223> OTHER INFORMATION: Oligonucleotide primer

<400> SEQUENCE: 8
ttgcaagtcc cgattggtaa gcaagc            26

<210> SEQ ID NO 9
<211> LENGTH: 26
<212> TYPE: DNA
<213> ORGANISM: Maize
<220> FEATURE:
<221> NAME/KEY: misc_feature
<222> LOCATION: (1)..(26)
<223> OTHER INFORMATION: Oligonucleotide primer

<400> SEQUENCE: 9
atcttcgatt ggtagaagtg agtccg            26